US012728090B1

(12) United States Patent
Coffey et al.

(10) Patent No.: US 12,728,090 B1
(45) Date of Patent: Sep. 8, 2026

(54) EYE FORMULATIONS

(71) Applicant: BAUSCH + LOMB IRELAND LIMITED, Dublin (IE)

(72) Inventors: Martin J. Coffey, Pittsford, NY (US); Maureen Koo, La Puente, CA (US)

(73) Assignee: BAUSCH + LOMB IRELAND LIMITED, Dublin (IE)

( * ) Notice: Subject to any disclaimer, the term of this patent is extended or adjusted under 35 U.S.C. 154(b) by 424 days.

(21) Appl. No.: 18/357,577

(22) Filed: Jul. 24, 2023

Related U.S. Application Data

(60) Provisional application No. 63/392,012, filed on Jul. 25, 2022.

(51) Int. Cl.

| | |
|---|---|
| ***A61K 36/00*** | (2006.01) |
| ***A61K 8/19*** | (2006.01) |
| ***A61K 8/26*** | (2006.01) |
| ***A61K 8/29*** | (2006.01) |
| ***A61K 8/49*** | (2006.01) |
| ***A61K 8/67*** | (2006.01) |
| ***A61K 8/92*** | (2006.01) |
| ***A61K 8/9789*** | (2017.01) |
| ***A61Q 1/14*** | (2006.01) |
| ***A61Q 19/10*** | (2006.01) |

(52) U.S. Cl.
CPC .............. *A61K 8/9789* (2017.08); *A61K 8/19* (2013.01); *A61K 8/26* (2013.01); *A61K 8/29* (2013.01); *A61K 8/4953* (2013.01); *A61K 8/673* (2013.01); *A61K 8/675* (2013.01); *A61K 8/676* (2013.01); *A61K 8/678* (2013.01); *A61K 8/922* (2013.01); *A61Q 1/14* (2013.01); *A61Q 19/10* (2013.01); *A61K 2800/30* (2013.01)

(58) Field of Classification Search
CPC ........................................................ A61Q 1/14
See application file for complete search history.

(56) References Cited

U.S. PATENT DOCUMENTS

2011/0251273 A1* 10/2011 Oddos .................... A61P 17/10 514/725

FOREIGN PATENT DOCUMENTS

KR 102342731 B1 * 12/2021 ............ C11D 3/382

* cited by examiner

*Primary Examiner* — Qiuwen Mi
(74) *Attorney, Agent, or Firm* — Finnegan, Henderson, Farabow, Garrett & Dunner LLP

(57) ABSTRACT

The present disclosure is related to eye formulations, such as gel-creams for use on the skin around the eyes, lash and brow serums for use on eyelash and/or eyebrows, and cleansing formulations for removing makeup and cleaning the eye area. The eye formulations include eye illuminating formulations and eye conditioning formulations comprising at least one preservative that does not induce dermal sensitization of the skin to which it is applied.

14 Claims, No Drawings

EYE FORMULATIONS

This application claims the benefit of priority from U.S. Provisional Application No. 63/392,012, filed Jul. 25, 2022, which is incorporated herein by reference in its entirety.

The present disclosure is related to eye formulations, such as gel-creams for use on the skin around the eyes, lash and brow serums for use on eyelash and/or eyebrows, and cleansing formulations for removing makeup and cleaning the eye area. The formulations disclosed herein comprise at least one preservative that does not induce dermal sensitization of the skin to which it is applied. In some embodiments, the formulations pass a Repeated Insult Patch Test as described herein. In some embodiments, there is provided a gel-cream formulation. In some embodiments, there is provided a lash and brow formulation. In some embodiments, there is provided a micellar cleansing formulation. In some embodiments, the formulation is an eye illumination formulation. In some embodiments, the formulation is an eye conditioning formulation.

In some embodiments, the eye formulations brighten the skin of the eye region. In some embodiments, the eye formulations do not include any fragrance. In some embodiments, the eye formulations do not include any animal-derived ingredients. In some embodiments, the eye formulations do not include any petroleum-derived ingredients. In some embodiments, the eye formulations comprise at least one preservative that does not induce dermal sensitization of the skin to which it is applied, and do not include any fragrance, any petroleum-derived ingredient, or any animal-derived ingredient.

Also disclosed herein are methods for cleansing, cleaning, conditioning, illuminating, moisturizing, lubricating, soothing, calming, refreshing, whitening, lightening, and/or brightening the eyelid, periocular, and/or ocular surface tissues. Also disclosed herein are methods for treating, improving, or ameliorating inflammation; removing irritants, makeup, debris, crusting, and/or excess oil or secretions; maintaining eyelid hygiene; and/or treating, improving, and/or ameliorating blepharitis and symptoms thereof.

Definitions of certain terms as used in this application are provided below. Unless defined otherwise, all technical and scientific terms used herein have the normal and common meaning that would be commonly understood by one of ordinary skill in the art to which this disclosure belongs.

As used herein, "a," "an," and "the" refer to one or more (i.e., to at least one) of the grammatical object of the article.

The terms "subject," "individual," and the like, as used herein, are interchangeable and refer to any animal, which may be a human or a non-human animal.

As will be understood by one of ordinary skill in the art, when disclosed herein, each range includes all possible subranges as well as individual numerical values within that range. For example, a range of "1.0 to 5.0" includes and would be understood to specifically disclose subranges such as "1.0 to 3.0," "1.5 to 3.7," "2.1 to 4.3," etc., as well as all individual numbers within the disclosed range, for example, 1.0, 1.1, 1.2, 1.3, etc.

As noted above, in some embodiments, the present disclosure is related to eye illumination formulations. As used herein, "illumination" and/or "brightening" refers to a reduction in appearance of uneven tone/pigment or a brightening of dull skin. In some embodiments, illumination is evaluated by visual assessment and scoring of luminosity and evenness of tone of skin at baseline, i.e., before skin is exposed to the claimed eye formulation, and after a certain number of applications of the claimed eye formulation. For example, an illumination scoring scale may be used to score visual assessments of one or more properties of the skin, such as luminosity/brightness and evenness of skin tone.

The eye formulations disclosed herein comprise at least one preservative. In some embodiments, the preservative is chosen from potassium sorbate, polylysine, and alexidine hydrochloride. In some embodiments, the preservative is potassium sorbate. In some embodiments, the preservative is polylysine. In some embodiments, the preservative is alexidine hydrochloride. In some embodiments, the eye formulations do not comprise hydroxyacetophenone.

In some embodiments, the eye formulation further comprises at least one natural humectant. In some embodiments, the eye formulation further comprises at least one plant extract. In some embodiments, the eye formulation further comprises at least one buffer.

In some embodiments, the eye formulation comprises an eye formulation for the eye area, comprising natural humectants. In some embodiments, the eye formulation comprises an eye formulation for the eye area comprising vitamins. In some embodiments, the eye formulation is free of parabens. In some embodiments, the eye formulation is free of thiazolinones. In some embodiments, the eye formulation is free of formaldehyde-donor preservatives. In some embodiments, the eye formulation is free of polyethylene glycol (PEG) ingredients. In some embodiments, the eye formulation is free of PEG-containing ingredients.

In some embodiments, the natural humectant of the eye formulation is chosen from sodium hyaluronate and glycerin. In some embodiments, the natural humectant of the eye formulation is sodium hyaluronate. In some embodiments, the natural humectant of the eye formulation is glycerin. In some embodiment, the natural humectants of the eye formulation are sodium hyaluronate and glycerin.

In some embodiments, the eye formulation comprises at least one plant extract. In some embodiments, the at least one plant extract of the eye formulation is chosen from *Euphrasia officinalis* (eyebright) extract, *Glycyrrhiza glabra* (licorice) root extract, caffeine, *Gleditsia triacanthos* seed extract, and *Butyrospermum parkii* (shea) butter. In some embodiments, the at least one plant extract is *Euphrasia officinalis* (eyebright) extract. In some embodiments, the at least one plant extract is *Glycyrrhiza glabra* (licorice) root extract. In some embodiments, the at least one plant extract is caffeine. In some embodiments, the at least one plant extract is *Gleditsia triacanthos* seed extract. In some embodiments, the at least one plant extract is *Butyrospermum parkii* (shea) butter.

In some embodiments, the eye formulation comprises at least one vitamin. In some embodiments, the at least one vitamin is chosen from niacinamide (vitamin B3), panthenol (pro-vitamin B5), biotin (vitamin B7), ascorbate (vitamin C), tetrahexyldecyl ascorbate (vitamin C), sodium ascorbyl phoaphate (vitamin C), and tocopheryl acetate (vitamin E). In some embodiments, the at least one vitamin is niacinamide (vitamin B3). In some embodiments, the at least one vitamin is panthenol (pro-vitamin B5). In some embodiments, the at least one vitamin is biotin (vitamin B7). In some embodiments, the at least one vitamin is ascorbate (vitamin C). In some embodiments, the at least one vitamin is tetrahexyldecyl ascorbate (vitamin C). In some embodiments, the at least one vitamin is sodium ascorbyl phosphate (vitamin C). In some embodiments, the at least one vitamin is tocopheryl acetate (vitamin E).

In some embodiments, the eye formulation comprises at least one buffer. In some embodiment, the eye formulation comprises a citrate-phosphate buffer. In some embodiments, the at least one buffer provides the eye formulation with a pH of about 7-8. In some embodiments, the at least one buffer provides the eye formulation with a pH of about 7. In some embodiments, the at least one buffer provides the eye formulation with a pH of about 8.

In some embodiments, the at least one buffer provides the eye formulation with a pH of about 7. In some embodiments, the at least one buffer provides the eye formulation with a pH of about 7.0, about 7.1, about 7.2, about 7.3, about 7.4, about 7.5, about 7.6, about 7.7, about 7.8, about 7.9, or about 8.0. In some embodiments, the pH of the liquid may be measured before being placed into the packaging. In some embodiments, the at least one buffer provides the eye formulation with a pH of 7.0, 7.1, 7.2, 7.3, 7.4, 7.5, 7.6, 7.7, 7.8, 7.9, or 8.0.

In some embodiments, the eye formulation comprises: water (aqua), niacinamide (vitamin B3), glycerin, alumina, synthetic fluorphlogopite, titanium dioxide, tin oxide, potassium sorbate, disodium EDTA (dihydrate), sodium hyaluronate (MMW), sodium acrylates copolymer, lecithin, *butyrospermum parkii* (shea) butter, squalene, dimethicone, panthenol (pro-vitamin B5), tocopheryl acetate (vitamin E), 1,2-hexanediol, caprylyl glycol, *Glycyrrhiza glabra* (licorice) root extract, tetrahexyldecyl ascorbate (vitamin C), *Gleditsia triacanthos* seed extract, caffeine, *Euphrasia officinalis* (eyebright) extract, mannitol, and ergothioneine.

In some embodiments, the eye formulation comprises about 77.5% w/w water (aqua), about 3.0% w/w niacinamide (vitamin B3), about 2.0% w/w glycerin, about 1.0% w/w alumina, about 0.5% w/w of a mixture of synthetic fluorphlogopite (65%), titanium dioxide (35%), and tin oxide (<2%), about 0.12% w/w potassium sorbate, about 0.1% w/w disodium EDTA (dihydrate), about 0.01% w/w sodium hyaluronate (MMW), about 2.0% w/w of a mixture of sodium acrylates copolymer (75%) and lecithin (25%), about 3.5% w/w *butyrospermum parkii* (shea) butter, about 2.0% w/w squalene, about 0.5% w/w dimethicone, about 0.1% w/w panthenol (pro-vitamin B5), about 0.1% w/w tocopheryl acetate (vitamin E), about 0.5% w/w 1,2-hexanediol, caprylyl glycol, about 0.01% w/w *Glycyrrhiza glabra* (licorice) root extract, about 3.0% w/w tetrahexyldecyl ascorbate (vitamin C), about 3.0% w/w *Gleditsia triacanthos* seed extract, about 0.5% w/w caffeine, about 0.5% w/w *Euphrasia officinalis* (eyebright) extract, and about 0.1% w/w of a mixture of mannitol and ergothioneine.

In some embodiments, the eye formulation comprises 77.5% w/w water (aqua), 3% w/w niacinamide (vitamin B3), 2% w/w glycerin, 1% w/w alumina, 0.5% w/w of a mixture of synthetic fluorphlogopite (65%), titanium dioxide (35%), and tin oxide (<2%), 0.1% w/w potassium sorbate, 0.1% w/w disodium EDTA (dihydrate), 0.01% w/w sodium hyaluronate (MMW), 2% w/w of a mixture of sodium acrylates copolymer (75%) and lecithin (25%), about 3.5% w/w *butyrospermum parkii* (shea) butter, about 2% w/w squalene, about 0.5% w/w dimethicone, about 0.1% w/w panthenol (pro-vitamin B5), about 0.1% w/w tocopheryl acetate (vitamin E), about 0.5% w/w 1,2-hexanediol, caprylyl glycol, about 0.01% w/w *Glycyrrhiza glabra* (licorice) root extract, about 3% w/w tetrahexyldecyl ascorbate (vitamin C), about 3% w/w *Gleditsia triacanthos* seed extract, about 0.5% w/w caffeine, about 0.5% w/w *Euphrasia officinalis* (eyebright) extract, and about 0.1% w/w of a mixture of mannitol and ergothioneine.

In some embodiments, the eye formulation comprises water (aqua), glycerin, 1,2-hexanediol, caprylyl glycol, dipotassium glycyrrhizate, disodium EDTA (dibydrate), polylysine, sodium hyaluronate (MMW), myristoyl pentapeptide-17, *Euphrasia officinalis* (eyebright) extract, pentylene glycol, *Isochrysis galbana* extract, panthenol (provitamin B5), tetrahexyldecyl ascorbate (vitamin C), tocopheryl acetate (vitamin E), botin (vitamin B7), sodium acrylates copolymer, and lecithin.

In some embodiments, the eye formulation comprises: about 91% w/w water (aqua), about 0.5% w/w glycerin, about 0.4% w/w 1,2-hexanediol, caprylyl glycol, about 0.2% w/w dipotassium glycyrrhizate, about 0.1% w/w disodium EDTA (dihydrate), about 0.004% w/w polylysine, about 0.1% w/w sodium hyaluronate (MMW), about 5.0% w/w myristoyl pentapeptide-17, about 0.5% w/w *Euphrasia officinalis* (eyebright) extract, about 0.2% w/w of a mixture of pentylene glycol and *Isochrysis galbana* extract, about 0.1% w/w panthenol (pro-vitamin B5), about 0.1% w/w tetrahexyldecyl ascorbate (vitamin C), about 0.1% w/w tocopheryl acetate (vitamin E), about 0.05% w/w biotin (vitamin B7), and about 1.6% w/w of a mixture of sodium acrylates copolymer (75%) and lecithin (25%).

In some embodiments, the eye formulation comprises: 91% w/w water (aqua), 0.5% w/w glycerin, 0.4% w/w 1,2-hexanediol, caprylyl glycol, 0.2% w/w dipotassium glycyrrhizate, 0.1% w/w disodium EDTA (dihydrate), 0.004% w/w polylysine, 0.1% w/w sodium hyaluronate (MMW), 5% w/w myristoyl pentapeptide-17, 0.5% w/w *Euphrasia officinalis* (eyebright) extract, 0.2% w/w of a mixture of pentylene glycol and *Isochrysis galbana* extract, 0.1% w/w panthenol (pro-vitamin B5), 0.1% w/w tetrahexyldecyl ascorbate (vitamin C), 0.1% w/w tocopheryl acetate (vitamin E), 0.05% w/w biotin (vitamin B7), and 1.6% w/w of a mixture of sodium acrylates copolymer (75%) and lecithin (25%).

In some embodiments, the eye formulation comprises water (aqua), isohexadecane, squalane, glycerin, niacinamide (vitamin B3), sodium ascorbyl phosphate (vitamin C), sodium hyaluronate (MMW), decyl glucoside, panthenol (pro-vitamin B5), sodium chloride USP, potassium chloride USP, sodium citrate USP dihydrate, disodium EDTA (dihydrate), *Glycyrrhiza glabra* (licorice) root extract, *Euphrasia officinalis* (eyebright) extract, citric acid USP, anhydrous, and alexidine hydrochloride.

In some embodiments, the eye formulation comprises about 90% w/w water (aqua), about 5.6% w/w isohexadecane, about 1.9% w/w squalane, about 0.7% w/w glycerin (plus about <0.19% w/w glycerin as a component in plant extracts), about 0.7% w/w niacinamide (vitamin B3), about 0.3% w/w sodium ascorbyl phosphate (vitamin C), about 0.1% w/w sodium hyaluronate (MMW), about 0.1% w/w decyl glucoside, about 0.1% w/w panthenol (pro-Vitamin B5), about 0.1% w/w sodium chloride USP, about 0.1% w/w potassium chloride USP, about 0.1% w/w sodium citrate USP dihydrate, about 0.1% w/w disodium EDTA (dihydrate), about <0.1% w/w *Glycyrrhiza glabra* (licorice) root extract, about <0.1% w/w *Euphrasia officinalis* (eyebright) extract, about 0.02% w/w citric acid USP, anhydrous, and about 0.001% w/w alexidine hydrochloride.

In some embodiments, the eye formulation comprises 90% w/w water (aqua), 5.6% w/w isohexadecane, 1.9% w/w squalane, 0.7% w/w glycerin (plus about <0.19% w/w glycerin as a component in plant extracts), 0.7% w/w niacinamide (vitamin B3), 0.3% w/w sodium ascorbyl phosphate (vitamin C), 0.1% w/w sodium hyaluronate (MMW), 0.1% w/w decyl glucoside, 0.1% w/w panthenol (pro-Vitamin B5), 0.1% w/w sodium chloride USP, 0.1% w/w potassium chloride USP, 0.1% w/w sodium citrate USP dihydrate, 0.1% w/w disodium EDTA (dihydrate), <0.1% w/w *Glycyrrhiza glabra* (licorice) root extract, <0.1% w/w *Euphrasia*

*officinalis* (eyebright) extract, 0.02% w/w citric acid USP, anhydrous, and 0.001% w/w alexidine hydrochloride.

In some embodiments, the eye formulations disclosed herein are free of parabens, thiazolinones, and formaldehyde-donor preservatives. In some embodiments, eye formulations disclosed herein are free of polyethylene glycol (PEG) and PEG-containing ingredients. In some embodiments, eye formulations disclosed herein are micellar cleansing formulas. In some embodiments, eye formulations disclosed herein are pH-balanced and non-irritating. In some embodiments, the eye formulations are eye illumination formulations. In some embodiments, the eye formulations are eye conditioning formulations.

The eye formulation disclosed herein may be prepared according to any known method for the manufacture of cosmetic formulations or preparations. As will be appreciated by those of ordinary skill in the art, a number of methods are known.

In some embodiments, the eye formulations disclosed herein are non-sterile liquid multi-use formulations, and are suitable for use with wipes, cloths, tissues, pads, or otherwise suitable material. In some embodiments, the wipes are formed from an absorbent material, and include pads, swabs, tissues, cottonwool, washcloths, and fiber applicators of any kind that are able to absorb the eye formulation and then be applied to the skin surface to clean, condition, illuminate, moisturize, lubricate, soothe, calm, refresh, whiten or brighten, and remove material on the skin.

In some embodiments, the eye formulations disclosed herein are useful for cleansing, cleaning, conditioning, illuminating, moisturizing, lubricating, soothing, calming, refreshing, whitening, lightening, and/or brightening the eyelid, periocular, and ocular surface tissues. In some embodiments, eye formulations disclosed herein are useful for treating, improving, and/or ameliorating inflammation; removing irritants, makeup, debris, crusting, excess oil and/or secretions; maintaining eyelid hygiene; and/or treating, improving, and/or ameliorating blepharitis and symptoms thereof. In some embodiments, eye formulations disclosed herein are suitable for adults, children, and contact-lens wearers.

Accordingly, provided herein are methods of cleansing, cleaning, conditioning, illuminating, moisturizing, lubricating, soothing, calming, refreshing, whitening, lightening, and/or brightening the eyelid, periocular, and/or ocular surface tissues, comprising applying to said eyelid, periocular, and/or ocular surface tissues an eye formulation or wipe pre-moistened with the eye formulation as disclosed herein. In some embodiments, provided herein are methods of treating, improving, and/or ameliorating inflammation; removing irritants, makeup, debris, crusting, and/or excess oil and/or secretions; maintaining eyelid hygiene; and/or treating, improving, or ameliorating blepharitis and symptoms thereof. The methods comprise applying to eyelid, periocular, and/or ocular surface tissues an eye formulation or wipe pre-moistened with the eye formulation as disclosed herein.

EXAMPLES

The present disclosure describes three cosmetic formulations that are designed to be used together as part of a cosmetic regimen to beatify, illuminate, and/or condition the eyes and the facial region surrounding the eyes.

Three cosmetic formulations designed and discussed here include: (i) a gel-cream formulation for use around the eyes; (ii) a lash and brow serum formulation for use on the eyelash and eyebrow region; and (iii) a micellar cleanser formulation for removing makeup and cleaning the face around the eyes.

Example 1: a Brightening/Illuminating Gel-Cream Formulation

Two brightening/illuminating gel-cream formulations were prepared. The compositions of the gel-cream formulations are shown in Table 1.

TABLE 1

Composition of Brightening/Illuminating Gel-Cream Formulations

| Phase | INCI | Formulation A (% w/w) | Formulation B (% w/w) |
|---|---|---|---|
| A | Water (aqua) | 77.08 | 77.46 |
| | Niacinamide (Vitamin B3) | 3.00 | 3.00 |
| | Glycerin | 2.00 | 2.00 |
| | Alumina | 1.00 | 1.00 |
| | Synthetic Fluorphlogopite (65%) | 0.50 | 0.50 |
| | Titanium Dioxide (35%) | | |
| | Tin Oxide (<2%) | | |
| | Hydroxyacetophenone | 0.50 | — |
| | Potassium Sorbate | — | 0.12 |
| | Disodium EDTA (dihydrate) | 0.10 | 0.10 |
| | Sodium Hyaluronate (MMW) | 0.01 | 0.01 |
| B | Sodium Acrylates Copolymer (75%) | 2.00 | 2.00 |
| | Lecithin (25%) | | |
| C | *Butyrospermum Parkii* (Shea) Butter | 3.50 | 3.50 |
| | Squalane | 2.00 | 2.00 |
| | Dimethicone | 0.50 | 0.50 |
| | Panthenol (pro-Vitamin B5) | 0.10 | 0.10 |
| | Tocopheryl acetate (Vitamin E) | 0.10 | 0.10 |
| D | 1,2-Hexanediol | 0.50 | 0.50 |
| | Caprylyl glycol | | |
| | Water | 0.01 | 0.01 |
| | Glycerin | | |
| | *Glycyrrhiza glabra* (Licorice) Root Extract | | |
| E | Tetrahexyldecyl Ascorbate (Vitamin C) | 3.00 | 3.00 |
| | Water | 3.00 | 3.00 |
| | Glycerin | | |
| | Gleditsia Triacanthos Seed Extract | | |
| | Caffeine | 0.50 | 0.50 |
| | Water | 0.50 | 0.50 |
| | Glycerin | | |
| | *Euphrasia Officinalis* (Eyebright) Extract | | |
| | Mannitol and Ergothioneine | 0.10 | 0.10 |

Manufacturing Process for Gel-Cream Formulation:

Step 1: Preparation of Phase A—Purified water was added to a main manufacturing vessel and agitation began with a propeller mixer. The ingredients from Phase A were added one by one, with mixing between each addition to ensure dissolution of the ingredients and the formation of a homogenous solution was achieved.

Step 2: Preparation of Phase B—The ingredients from Phase B were added to the main manufacturing vessel, while continuously mixing the mixture. Mixing was continued until proper hydration was achieved. The mixture was heated to about 60° C. to about 65° C. with continuous mixing.

Step 3: Preparation of Phase C—The Phase C ingredients were weighed and added to an appropriately sized vessel, and then heated to about 60° C. to about 65° C. Mixing was continued until all the ingredients were dissolved and a clear liquid was achieved.

Step 4: Direct emulsification—On completion of steps 2 and 3, the Phase C mixture was added in the main vessel containing Phase B. The combined mixtures were mixed with high-sheer homogenization and side scraping, until the combined mixture was homogenous.

Step 5: Cooling—On completion of step 4, the homogenization was stopped and the combined mixture was returned to propeller mixing. The combined mixture was then cooled to about 40° C.

Step 6: Phase D Premix—The Licorice PT-40 and Symdiol 68 were transferred to an appropriately sized vessel and heated to about 40° C. The ingredients were stirring together, continuously, for about 30 minutes. When a uniform clear solution was achieved, the mixture was added to the main vessel at about 40° C.

Step 7: Addition of Phase E—When main vessel reached a temperature of about 40° C. or below, each one of the Phase E ingredients were added. Between each addition, the mixture was mixed until it was homogenous. The final mixture was then allowed to cool down.

Step 8: Final mixing—The cooled down mixture was then finally mixed for about 15 minutes, and the temperature was maintained below about 34° C. The mixing was then stopped a sample was taken from the top and the bottom of the vessel. The pH of the samples were measured and found to be in the range of about 5.3 to about 6.3.

Example 2: Repeated Insult Patch Test (RIPT) for a Brightening/Illuminating Gel-Cream Formulation Gel-cream formulations were tested to determine whether, as a result of repeated applications, the eye formulations induce dermal sensitization in human subjects using a Repeated Insult Patch Test (RIPT).

As shown above, Formulations A and B contained different preservatives. Formulation A was preserved using Symsave H (hydroxyacetophenone), which is claimed to be a safe, non-sensitizing preservative for use in cosmetics. Formulation B was preserved using potassium sorbate. Formulation A failed a Repeated Insult Patch Test (RIPT), while Formulation B passed the RIPT.

Formulation A Test Results:

A modified human repeat insult patch test (RIPT) was conducted to evaluate Formulation A as a result of repeated applications, to induce dermal sensitization in humans. A total of 111 subjects completed the induction phase and 106 subjects completed the challenge phase.

For the induction period, subjects were semi-occlusively patched with approximately 200 microliters of Formulation A test material, approximately 200 microliters of 0.5% Sodium Lauryl Sulfate (SLS) to serve as the positive control, and a blank patch to serve as the negative control, 9 times at approximately 48 to 72-hour intervals. Subjects removed the patches approximately 48 hours after each application, or 2 hours prior to a study visit, and sites were graded approximately 48 to 72 hours after each. After 9-12 days of no patching ("rest period"), challenge patches (test material only, the controls were not challenged) were applied to alternative (naïve) sites. A technician removed the challenge patches approximately 48 hours after application. Reactions at alternative (naïve) sites were graded approximately 48, 72, and 96 hours after application.

More than 1 subject showed an allergic response, therefore rechallenge was conducted on selected subjects using selected ingredients of the formulation. Significant (edematous) reactions were exhibited by 3 of the 7 rechallenge subjects to Symsave H 979940 (Hydroxyacetophenone)—20%. Significant (edematous) reactions were exhibited by 4 of the 7 rechallenge subjects to Symsave H 979940 (Hydroxyacetophenone)—50%.

The following scales and symbols were used to grade the test sites during the induction phase: Induction Phase Grading Scale:

Erythema and Elevated Responses

0 No evidence of irritation
1 Minimal erythema, barely perceptible
2 Definite erythema, readily visible; or minimal edema; or minimal papular response
3 Erythema and papules
4 Definite edema
5 Erythema, edema, and papules
6 Vesicular eruption
7 Strong reaction spreading beyond test site Effects on Superficial Layers of the Skin A 0 Slight glazed appearance
B 1 Marked glazing
C 2 Glazing with peeling and cracking
D 3 Glazing with fissures
E 3 Film of dried serous exudate covering all or portion of the patch site
F 3 Small petechial erosions and/or scabs Letter grade numerical equivalents (ie, A=0; B=1; C=2; and D, E, and F=3) were added to the numerical scores (e.g., 2C=2+2=4). Any single or combined score of 3 or higher was considered to be a 3 for the remainder of the test, and applications for that test site were relocated to an alternate site.

The following scales and symbols were used to grade the test sites during the challenge phase: Challenge Grading Scale Erythema Scale: This scale was used only for grading degree of erythema (redness).

0 No visible erythema
1 Mild erythema (faint pink to definite pink)
2 Moderate erythema (definite redness)
3 Severe erythema (very intense redness)

Elevated Responses: Edema, papules, vesicles, and bullae, if present, were graded as independent responses.

E Edema—definite swelling
P Papules—small, red, solid elevations; surface of reaction has granular feeling Table 2 presents the converted numerical and letter score frequencies for Formulation A at each grading time point during the induction and challenge phases. (Note: 48H=48-hour observation, 72H=72-hour observation, and 96H=96-hour observation.)

TABLE 2

Summary of Reactions for brightening/illuminating gel-cream Formulation A

| Reaction | Induction Reading | | | | | | | | | Challenge Reading | | |
|---|---|---|---|---|---|---|---|---|---|---|---|---|
| Score | G1 | G2 | G3 | G4 | G5 | G6 | G7 | G8 | G9 | 48H | 72H | 96H |
| 0 | 97 | 84 | 88 | 84 | 78 | 77 | 77 | 72 | 77 | 101 | 85 | 88 |
| 1 | 12 | 20 | 15 | 14 | 18 | 17 | 19 | 21 | 18 | 3 | 16 | 15 |
| 2 | 1 | 6 | 7 | 13 | 12 | 14 | 12 | 16 | 13 | 0 | 3 | 1 |
| 3 | 1 | 1 | 0 | 0 | 1 | 1 | 1 | 0 | 2 | | | |
| 4 | 0 | 0 | 0 | 0 | 0 | 0 | 0 | 1 | 0 | | | |
| 5 | 0 | 0 | 1 | 0 | 0 | 0 | 0 | 0 | 0 | | | |
| 6 | 0 | 0 | 0 | 0 | 1 | 1 | 1 | 0 | 0 | | | |
| 8 | 0 | 0 | 0 | 0 | 1 | 1 | 0 | 0 | 0 | | | |
| 9 | 0 | 0 | 0 | 0 | 0 | 0 | 1 | 1 | 0 | | | |

TABLE 2-continued

| Summary of Reactions for brightening/illuminating gel-cream Formulation A | | | | | | | | | | | | |
|---|---|---|---|---|---|---|---|---|---|---|---|---|
| Reaction | Induction Reading | | | | | | | | | Challenge Reading | | |
| Score | G1 | G2 | G3 | G4 | G5 | G6 | G7 | G8 | G9 | 48H | 72H | 96H |
| 2EP | | | | | | | | | | 1 | 0 | 0 |
| 3E | | | | | | | | | | 0 | 0 | 1 |
| NA[a] | | | | | | | | | | 1 | 0 | 1 |

[a]NA-Not patched for subject 15

Formulation B: Test Results

Methodology: A total of 236 subjects were enrolled; 201 subjects completed the test. No subject discontinued due to test material reaction. Of the 201 subjects who completed the test, 49 were male and 152 were female. The subjects ranged in age from 18 to 70.

Method: Induction Phase: A webril/adhesive patch was used semi-occlusively. Approximately 0.2 μm of the Test Material was applied to each patch. As per Standard Operating Procedures (SOP), the left side of the back was usually the test area for the Induction Phase. The subject's skin was marked with a surgical marker at the left side of the test site. The test site was recorded on the anatomical diagram of each subject's individual Data Form. In addition, at that time, the prospective placement of the Challenge test site was also recorded on the anatomical diagram.

Each subject was instructed that the patch was to remain in place and kept dry for approximately 24 hours, at which time the patch was to be removed by the subject. An approximately 24-hour period, during which no test material was applied, followed the weekday patch removals; an approximately 48-hour period followed the weekend patch removals.

Each subject returned on the appropriate day. The test site was observed by the technician, and the reaction scored and recorded (see Scoring system, below). The identical test site was then repatched until nine (9) Induction patchings were completed.

In accordance with the SOP, if a subject was unable to make up a missed patching during the same week, the subject was either patched four days the following week or was patched at the end of the Induction Phase. Any absences and make-up days are noted by the dates on the individual Data Form.

A series of nine (9) Induction patchings was completed over a period of approximately three weeks.

Rest Period: A Rest Period of approximately two weeks followed the last Induction patching; no test material was applied during the Rest Period. Subjects were instructed to provide notification if they experienced any reaction during the Rest Period.

Challenge Phase: At the Challenge Phase, the original Induction test site was observed and each subject queried as to whether any reaction was experienced during the Rest Period. Any reactions were recorded on the Data Form. A webril/adhesive patch was used semi-occlusively. Approximately 0.2 μm of the Test Material was applied to each patch. As per the RIPT SOP, the opposite side of the back was usually the virgin test site for the Challenge Phase.

As per the RIPT SOP, the Challenge patch was applied to the virgin site only. Each subject was again instructed to keep the patch on and dry.

Each subject returned approximately 24 hours later (Challenge Reading 1), at which time the patch was removed and the Challenge site scored and recorded by the technician. The original test site was also observed. (See Results, below.)

Each subject returned at approximately 48 hours (Challenge Reading 2), approximately 72 hours (Challenge Reading 3) and approximately 96 hours (Challenge Reading 4) post-patching for additional observations; reactions were scored and recorded.

Scoring system: See Table 3 below. The test sites were scored using the modified scoring scale of the International Contact Dermatitis Research Group System: Fisher, Alexander A., Contact Dermatitis, Lea & Febiger, Philadelphia, 2008: p 27.

Results: See Table 3 below. No adverse reactions or adverse events related to the Test Material were exhibited/reported by any subject during this test. Erythema, edema, dryness, staining, peeling and hyperpigmentation/hypopigmentation are possible, expected endpoints and not considered Adverse Reactions. This test was conducted under the supervision of a Board-Certified Dermatologist, a Co-Investigator. At Challenge Reading 3, the Dermatologist participated in the scoring of the subjects.

No adverse reactions or adverse events were reported/observed in any of the subjects. During the Induction Phase, two subjects exhibited low-level (±/1) reactions. During the Challenge, one other subject exhibited a low level (±/1) reaction.

Conclusion: In this Repeated Insult Patch Test, eye gel cream Formulation B, did not induce dermal sensitization in human subjects.

TABLE 3

| Summary of Reactions for brightening/illuminating gel-cream Formulation B | | | | | | | | | | | | | |
|---|---|---|---|---|---|---|---|---|---|---|---|---|---|
| Reaction | Induction Reading | | | | | | | | | Challenge Reading | | | |
| Grade | 1 | 2 | 3 | 4 | 5 | 6 | 7 | 8 | 9 | 1 | 2 | 3 | 4 |
| 0 | 221 | 214 | 211 | 211 | 208 | 207 | 206 | 206 | 206 | 201 | 196 | 201 | 200 |
| ± | | 2 | 1 | | | | | | | | 1 | | |
| 1 | 1 | | | | | | | | | 1 | | | |
| 1E | | | | | | | | | | | | | |
| 2 | | | | | | | | | | | | | |
| 2E | | | | | | | | | | | | | |
| 3E | | | | | | | | | | | | | |
| 4E | | | | | | | | | | | | | |
| — | | | | | | | | | | | 4 | | 1 |
| N9R | | | | | | | | | | | | | |
| Total | 222 | 216 | 212 | 211 | 208 | 207 | 206 | 206 | 206 | 202 | 201 | 201 | 201 |

Scoring System:

0=No visible reaction
+=Faint, minimal erythema
1=Erythema
2=Intense erythema, induration
3=Intense erythema, induration, vesicles
4=Severe reaction with erythema, induration, vesicles, pustules (may be weeping)
E=Edema
−=No reading
N9R=No 9th reading Example 3: Lash and Brow Serum Formulation Two lash and brow serum formulations were prepared. The compositions of the lash and brow serum formulations are shown in Table 4.

TABLE 4

Composition of Lash and Brow Serum Formulations

| Phase | INCI | Formulation C (% w/w) | Formulation D (% w/w) |
|---|---|---|---|
| A | Water (aqua) | 91.550 | 91.046 |
| | Glycerin | 0.500 | 0.500 |
| | 1,2-Hexanediol | 0.400 | 0.400 |
| | Caprylyl glycol | | |
| | Dipotassium Glycyrrhizate | 0.200 | 0.200 |
| | Disodium EDTA (dihydrate) | 0.100 | 0.100 |
| | Hydroxyacetophenone | 0.500 | — |
| | Polylysine | — | 0.004 |
| B | Sodium Hyaluronate (MMW) | 0.100 | 0.100 |
| C | Water | 5.000 | 5.000 |
| | Glycerin | | |
| | Myristoyl Pentapeptide-17 | | |
| | Water | 0.500 | 0.500 |
| | Glycerin | | |
| | *Euphrasia Officinalis* (Eyebright) Extract | | |
| | Pentylene Glycol | 0.200 | 0.200 |
| | Isochrysis Galbana Extract | | |
| | Panthenol (pro-Vitamin B5) | 0.100 | 0.100 |
| | Tetrahexyldecyl Ascorbate (Vitamin C) | 0.100 | 0.100 |
| | Tocopheryl acetate (Vitamin E) | 0.100 | 0.100 |
| | Biotin (Vitamin B7) | 0.050 | 0.050 |
| D | Sodium Acrylates Copolymer (75%) | 1.600 | 1.600 |
| | Lecithin (25%) | | |

Manufacturing Process for Lash and Brow Serum

Step 1: Preparation of Phase A—Purified Water was added to a main vessel and agitated with a propeller mixer. The ingredients from Phase A were added one by one with mixing between each addition, until the ingredient was dissolved and homogenous solution was obtained.

Step 2: Addition of Phase B—Sodium Hyaluronate Powder was added to the vessel, and mixed in until it was sufficiently dispersed.

Step 3: Addition of Phase C—The Phase C ingredients were added to the main vessel, one by one, with mixing between each addition, until the ingredients were dissolved and homogenous solution was obtained.

Step 4: Addition of Phase D—Lecigel was added to the main vessel, and mixed until it was sufficiently dispersed and hydrated and a homogenous mixture was achieved.

Example 4: Repeated Insult Patch Test (RIPT) for a Lash and Brow Serum Formulation Lash and Brow serum formulations were tested to determine whether, as a result of repeated applications, the formulations induce dermal sensitization in human subjects using a Repeated Insult Patch Test (RIPT).

As shown above, Formulations C and D contained different preservatives. Formulation C was preserved using Symsave H (hydroxyacetophenone) which is claimed to be a safe, non-sensitizing preservative for use in cosmetics. Formulation D was preserved using epsilon-polylysine as a preservative. Formulation C failed a RIPT, which formulation D passed the RIPT.

Formulation C Test Results:

A modified human repeat insult patch test (RIPT) was conducted to evaluate Formulation C as a result of repeated applications, to induce dermal sensitization in humans. A total of 111 subjects completed the induction phase and 106 subjects completed the challenge phase.

For the induction period, subjects were semi-occlusively patched with approximately 200 microliters of Formulation C test material, approximately 200 microliters of 0.5% Sodium Lauryl Sulfate (SLS) to serve as the positive control, and a blank patch to serve as the negative control, 9 times at approximately 48 to 72-hour intervals. Subjects removed the patches approximately 48 hours after each application, or 2 hours prior to a study visit, and sites were graded approximately 48 to 72 hours after each. After 9-12 days of no patching ("rest period"), challenge patches (test material only, the controls were not challenged) were applied to alternative (naïve) sites. A technician removed the challenge patches approximately 48 hours after application. Reactions at alternative (naïve) sites were graded approximately 48, 72, and 96 hours after application.

More than 1 subject showed an allergic response, therefore rechallenge was conducted on selected subjects using selected ingredients of the formulation. Significant (edematous) reactions were exhibited by 3 of the 7 rechallenge subjects to Symsave H 979940 (Hydroxyacetophenone)—20%. Significant (edematous) reactions were exhibited by 4 of the 7 rechallenge subjects to Symsave H 979940 (Hydroxyacetophenone)—50%.

The following scales and symbols were used to grade the test sites during the induction phase: Induction Phase Grading Scale:

Erythema and Elevated Responses

0 No evidence of irritation

1 Minimal erythema, barely perceptible

2 Definite erythema, readily visible; or minimal edema; or minimal papular response 3 Erythema and papules Effects on Superficial Layers of the Skin A 0 Slight glazed appearance B 1 Marked glazing C 2 Glazing with peeling and cracking D 3 Glazing with fissures E 3 Film of dried serous exudate covering all or portion of the patch site F 3 Small petechial erosions and/or scabs Letter grade numerical equivalents (ie, A=0; B=1; C=2; and D, E, and F=3) were added to the numerical scores (e.g., 2C=2+2=4). Any single or combined score of 3 or higher was considered to be a 3 for the remainder of the test, and applications for that test site were relocated to an alternate site.

The following scales and symbols were used to grade the test sites during the challenge phase: Challenge Grading Scale Erythema Scale: This scale was used only for grading degree of erythema (redness).

0 No visible erythema

1 Mild erythema (faint pink to definite pink)

2 Moderate erythema (definite redness)

3 Severe erythema (very intense redness)

Elevated Responses: Edema, papules, vesicles, and bullae, if present, were graded as independent responses.

E Edema—definite swelling

P Papules—small, red, solid elevations; surface of reaction has granular feeling Table 5 presents the converted numerical and letter score frequencies for Formulation A at each grading time point during the induction and challenge phases. (Note: 48H=48-hour observation, 72H=72-hour observation, and 96H=96-hour observation.)

TABLE 5

Summary of Reactions for Lash and Brow Serum Formulation C

| Reaction | Induction Reading | | | | | | | | | Challenge Reading | | |
|---|---|---|---|---|---|---|---|---|---|---|---|---|
| Score | G1 | G2 | G3 | G4 | G5 | G6 | G7 | G8 | G9 | 48H | 72H | 96H |
| 0 | 104 | 96 | 93 | 91 | 86 | 85 | 79 | 77 | 80 | 103 | 100 | 101 |
| 1 | 6 | 11 | 14 | 15 | 16 | 18 | 27 | 27 | 26 | 1 | 2 | 2 |
| 2 | 1 | 4 | 4 | 4 | 8 | 5 | 2 | 3 | 3 | 1 | 2 | 2 |
| 3 | 0 | 0 | 0 | 1 | 0 | 0 | 1 | 3 | 2 | | | |
| 5 | 0 | 0 | 0 | 0 | 1 | 2 | 1 | 0 | 0 | | | |
| 6 | 0 | 0 | 0 | 0 | 0 | 1 | 1 | 1 | 0 | | | |
| 2E | | | | | | | | | | 0 | 1 | 1 |
| 2EP | | | | | | | | | | 1 | 0 | 0 |
| 3E | | | | | | | | | | 0 | 1 | 0 |

Formulation D: Test Results

Methodology: A total of 236 subjects were enrolled; 201 subjects completed the test. No subject discontinued due to test material reaction.

Method: Induction Phase: A webril/adhesive patch was used semi-occlusively. Approximately 0.2 μm of the Test Material was applied to each patch. As per Standard Operating Procedures (SOP), the left side of the back was usually the test area for the Induction Phase. The subject's skin was marked with a surgical marker at the left side of the test site. The test site was recorded on the anatomical diagram of each subject's individual Data Form. In addition, at that time, the prospective placement of the Challenge test site was also recorded on the anatomical diagram.

Each subject was instructed that the patch was to remain in place and kept dry for approximately 24 hours, at which time the patch was to be removed by the subject. An approximately 24-hour period, during which no test material was applied, followed the weekday patch removals; an approximately 48-hour period followed the weekend patch removals.

Each subject returned on the appropriate day. The test site was observed, and the reaction scored and recorded (see Scoring system, below). The identical test site was then repatched until nine (9) Induction patchings were completed.

In accordance with the SOP, if a subject was unable to make up a missed patching during the same week, the subject was either patched four days the following week or was patched at the end of the Induction Phase. Any absences and make-up days are noted by the dates on the individual Data Form.

A series of nine (9) Induction patchings was completed over a period of approximately three weeks.

Rest Period: A Rest Period of approximately two weeks followed the last Induction patching; no test material was applied during the Rest Period. Subjects were instructed to notify SGS if they experienced any reaction during the Rest Period.

Challenge Phase: At the Challenge Phase, the original Induction test site was observed and each subject queried as to whether any reaction was experienced during the Rest Period. Any reactions were recorded on the Data Form. A webril/adhesive patch was used semi-occlusively. Approximately 0.2 μm of the Test Material was applied to each patch. As per the RIPT SOP, the opposite side of the back was usually the virgin test site for the Challenge Phase.

As per the RIPT SOP, the Challenge patch was applied to the virgin site only. Each subject was again instructed to keep the patch on and dry.

Each subject returned approximately 24 hours later (Challenge Reading 1), at which time the patch was removed and the Challenge site scored and recorded by the technician. The original test site was also observed. (See Results, below.)

Each subject returned at approximately 48 hours (Challenge Reading 2), approximately 72 hours (Challenge Reading 3) and approximately 96 hours (Challenge Reading 4) post-patching for additional observations; reactions were scored and recorded.

Scoring system: See Table 6, below. The test sites were scored using the modified scoring scale of the International Contact Dermatitis Research Group System: Fisher, Alexander A., Contact Dermatitis, Lea & Febiger, Philadelphia, 2008: p 27.

Results: See Table 6, below. No adverse reactions or adverse events related to the Test Material were exhibited/reported by any subject during this test. Erythema, edema, dryness, staining, peeling and hyperpigmentation/hypopigmentation are possible, expected endpoints and not considered Adverse Reactions. This test was conducted under the supervision of a Board-Certified Dermatologist, a Co-Investigator. At Challenge Reading 3, the Dermatologist participated in the scoring of the subjects. A total of 201 subjects completed the test; 49 male and 152 female. The subjects range in age from 18 to 70.

No adverse reactions or adverse events were reported/observed in any of the subjects. During the Induction Phase, two subjects exhibited low-level (±/1) reactions. During the Challenge, no reactions were exhibited.

Conclusion: In this Repeated Insult Patch Test, Lash and brow serum Formulation D, did not induce dermal sensitization in human subjects.

Table 6: Summary of reactions for Lash and brow serum Formulation D

Total number of subjects enrolled: 236; and total number of subjects completed: 201

| Reaction | Induction Reading | | | | | | | | | Challenge Reading | | | |
|---|---|---|---|---|---|---|---|---|---|---|---|---|---|
| Grade | 1 | 2 | 3 | 4 | 5 | 6 | 7 | 8 | 9 | 1 | 2 | 3 | 4 |
| 0 | 222 | 214 | 211 | 210 | 208 | 207 | 206 | 206 | 206 | 202 | 197 | 201 | 200 |
| ± | | 2 | | 1 | | | | | | | | | |
| 1 | | | 1 | | | | | | | | | | |
| 1E | | | | | | | | | | | | | |
| 2 | | | | | | | | | | | | | |
| 2E | | | | | | | | | | | | | |
| 3E | | | | | | | | | | | | | |
| 4E | | | | | | | | | | | | | |
| — | | | | | | | | | | | 4 | | 1 |
| N9R | | | | | | | | | | | | | |
| Total | 222 | 216 | 212 | 211 | 208 | 207 | 206 | 206 | 206 | 202 | 201 | 201 | 201 |

Scoring System:

0=No visible reaction

+=Faint, minimal erythema

1=Erythema

2=Intense erythema, induration

3=Intense erythema, induration, vesicles

4=Severe reaction with erythema, induration, vesicles, pustules (may be weeping)

E=Edema

−=No reading

N9R=No 9th reading

Example 5: Micellar Cleanser and Makeup Remover Formulation

A micellar water cleanser and makeup remover formulation was prepared. The composition is shown in Table 7.

TABLE 7

Composition for Micellar Cleanser and Makeup Remover formulation (Formulation E)

| INCI | % w/w |
|---|---|
| Water (aqua) | 90.022 |
| Isohexadecane | 5.556 |
| Squalane | 1.852 |
| Glycerin | 0.741 |
| Niacinamide (Vitamin B3) | 0.694 |
| Sodium ascorbyl phosphate (Vitamin C) | 0.278 |
| Sodium Hyaluronate (MMW) | 0.093 |
| Decyl glucoside | 0.093 |
| Panthenol (pro-Vitamin B5) | 0.093 |
| Sodium Chloride USP | 0.093 |
| Potassium Chloride USP | 0.093 |
| Sodium Citrate USP Dihydrate | 0.093 |
| Disodium EDTA (dihydrate) | 0.093 |
| Water | 0.093 |
| Glycerin | |
| *Glycyrrhiza glabra* (Licorice) Root Extract | |
| Water | 0.093 |
| Glycerin | |
| *Euphrasia Officinalis* (Eyebright) Extract | |
| Citric acid USP, anhydrous | 0.019 |
| Alexidine Hydrochloride | 0.001 |

Manufacturing Process for Micellar Cleanser and Makeup Remover

A 250 ppm alexidine solution was prepared by adding 250 mg alexidine to 1000 g purified water, and mixing until the alexidine dissolved. Water was added to the vessel at about 90% of batch weight. Mixing was initiated at 700 rpm using a lab mixer. Sodium chloride, potassium chloride, sodium citrate, and citric acid were added to the mixture. Sodium hyaluronate was dispersed in water and mixed for about 30 minutes to hydrate. Sodium ascorbyl phosphate was added to the mixture. Glycerin, panthenol, niacinamide, licorice root extract, and eyebright extract were added to the mixture. The 250 ppm alexidine, as prepared in step 1, was added to the mixture. Decyl glucoside surfactant was added. Mixing was continued for about 30 minutes. The pH of the mixture was checked and, if necessary, was adjusted with sodium hydroxide and/or hydrochloric acid to a pH of about 7.1. Water was added to the final mixture to obtain the final batch weight. The final mixture was mixed for about 15 minutes. The aqueous phase was filtered through a 0.45-micron or 0.2-micron filter to clarify or reduce bioburden.

In a separate vessel, the oil phase was prepared as a mixture of isohexadecane and squalane. (The isohexadecane is a slightly volatile oil so preparation and holding of the oil phase prior to filling should control and minimize possible evaporation of isohexadecane.) The ratio of the two oils was 3 parts isohexadecane to 1 part squalene. The isohexadecane was 6% of weight of aqueous phase and squalane was 2% of weight of aqueous phase.

Bottles were filled with a two-stage fill such that 92.6% by wt. in the bottle will be an aqueous layer and 7.4% by weight will be an oil layer. In other words, the weight of the oil phase was 8.0% of weight of aqueous phase. For example, for a 4 oz. fill (~113 g), 105.0 g of aqueous phase was filled first followed by 8.40 g of oil phase.

Example 6: Repeated Insult Patch Test (RIPT) for a Micellar Cleanser and Makeup Remover Formulation Micellar cleanser and makeup remover Formulation E was tested to determine whether, as a result of repeated applications, the formulation induces dermal sensitization in human subjects using a Repeated Insult Patch Test (RIPT).

Formulation E was prepared as shown above and subjected to a RIPT.

Methodology: A total of 236 subjects were enrolled; 201 subjects completed the test. No subject discontinued due to test material reaction.

Method: Induction Phase: A webril/adhesive patch was used semi-occlusively. Approximately 0.2 gm of the Test Material was applied to each patch. As per the Standard Operating Procedures (SOP), the left side of the back was usually the test area for the Induction Phase. The subject's skin was marked with a surgical marker at the left side of the test site. The test site was recorded on the anatomical diagram of each subject's individual Data Form. In addition, at that time, the prospective placement of the Challenge test site was also recorded on the anatomical diagram.

Each subject was instructed that the patch was to remain in place and kept dry for approximately 24 hours, at which time the patch was to be removed by the subject. An approximately 24-hour period, during which no test material was applied, followed the weekday patch removals; an approximately 48-hour period followed the weekend patch removals.

Each subject returned on the appropriate day. The test site was observed, and the reaction scored and recorded (see Scoring system, below). The identical test site was then repatched until nine (9) Induction patchings were completed.

In accordance with the SOP, if a subject was unable to make up a missed patching during the same week, the subject was either patched four days the following week or was patched at the end of the Induction Phase. Any absences and make-up days are noted by the dates on the individual Data Form.

A series of nine (9) Induction patchings was completed over a period of approximately three weeks.

Rest Period: A Rest Period of approximately two weeks followed the last Induction patching; no test material was applied during the Rest Period. Subjects were instructed to provide notification if they experienced any reaction during the Rest Period.

Challenge Phase: At the Challenge Phase, the original Induction test site was observed and each subject queried as to whether any reaction was experienced during the Rest Period. Any reactions were recorded on the Data Form. A webril/adhesive patch was used semi-occlusively. Approximately 0.2 μm of the Test Material was applied to each patch. As per the RIPT SOP, the opposite side of the back was usually the virgin test site for the Challenge Phase.

As per the RIPT SOP, the Challenge patch was applied to the virgin site only. Each subject was again instructed to keep the patch on and dry.

Each subject returned approximately 24 hours later (Challenge Reading 1), at which time the patch was removed and the Challenge site scored and recorded by the SGS technician. The original test site was also observed. (See Results, below.)

Each subject returned at approximately 48 hours (Challenge Reading 2), approximately 72 hours (Challenge Reading 3) and approximately 96 hours (Challenge Reading 4) post-patching for additional observations; reactions were scored and recorded.

Scoring system: See Table 8. The test sites were scored using the modified scoring scale of the International Contact Dermatitis Research Group System: Fisher, Alexander A., Contact Dermatitis, Lea & Febiger, Philadelphia, 2008: p 27.

Results: See Table 8, below. No adverse reactions or adverse events related to the Test Material were exhibited/reported by any subject during this test. Erythema, edema, dryness, staining, peeling and hyperpigmentation/hypopigmentation are possible, expected endpoints and not considered Adverse Reactions. This test was conducted under the supervision of a Board-Certified Dermatologist, a Co-Investigator. At Challenge Reading 3, the Dermatologist participated in the scoring of the subjects. A total of 201 subjects completed the test; 49 male and 152 female. The subjects range in age from 18 to 70.

No adverse reactions or adverse events were reported/observed in any of the subjects. During the Induction Phase, five subjects exhibited low-level (±/1) reactions. During the Challenge, one other subject exhibited a low level (±) reaction.

Conclusion: In this Repeated Insult Patch Test, the micellar cleanser and makeup remover Formulation E, did not induce dermal sensitization in human subjects.

Table 8: Summary of reactions for a micellar cleanser and makeup remover formulation Total number of subjects enrolled: 236; and total number of subjects completed: 201

| Reaction | Induction Reading | | | | | | | | | Challenge Reading | | | |
|---|---|---|---|---|---|---|---|---|---|---|---|---|---|
| Grade | 1 | 2 | 3 | 4 | 5 | 6 | 7 | 8 | 9 | 1 | 2 | 3 | 4 |
| 0 | 222 | 216 | 211 | 209 | 208 | 206 | 205 | 204 | 205 | 201 | 197 | 201 | 200 |
| ± | | | 1 | 1 | | 1 | 1 | 2 | 1 | 1 | | | |
| 1 | | | | 1 | | | | | | | | | |
| 1E | | | | | | | | | | | | | |
| 2 | | | | | | | | | | | | | |
| 2E | | | | | | | | | | | | | |
| 3E | | | | | | | | | | | | | |
| 4E | | | | | | | | | | | | | |
| — | | | | | | | | | | | 4 | | 1 |
| N9R | | | | | | | | | | | | | |
| Total | 222 | 216 | 212 | 211 | 208 | 207 | 206 | 206 | 206 | 202 | 201 | 201 | 201 |

Scoring System:

0=No visible reaction

+=Faint, minimal erythema

1=Erythema

2=Intense erythema, induration

3=Intense erythema, induration, vesicles

4=Severe reaction with erythema, induration, vesicles, pustules (may be weeping)

E=Edema

−=No reading

N9R=No 9th reading

Example 7: Cumulative Irritation Test (CIT)

The dermal irritation properties of the following test materials were compared in human subjects:

#1 Cumulative Irritation Test-Lash and Brow Serum Formulation C: Test as received; patch semiocclusively. Discard patches after 30 minutes.

#2 Cumulative Irritation Test-Eye Gel Cream Formulation B: Test as received; patch semi-occlusively. Discard patches after 30 minutes.

#3 Cumulative Irritation Test-Micellar makeup remover Formulation F: Test as received; patch semiocclusively. Discard patches after 30 minutes.

#4 Cumulative Irritation Test-Micellar makeup remover Formulation E: Test as received; patch semiocclusively. Discard patches after 30 minutes.

#5 Cumulative Irritation Test-Lash and Brow Serum Formulation D: Test as received; patch semiocclusively. Discard patches after 30 minutes.

#6 Olay for Bright Eyes: Test as received; patch semiocclusively. Discard patches after 30 minutes.

#7 Loreal Lash Serum Solution: Test as received; patch semi-occlusively. Discard patches after 30 minutes.

#8 Negative control—(Saline); Test as received; patch semi-occlusively. Discard patches after 30 minutes.

#9 Sodium Lauryl Sulfate: Dilute to 0.5% in distilled water prior to application to patches; prepare fresh daily. Patch semi-occlusively. Discard patches after 30 minutes.

Methodology: A total of 38 subjects were enrolled; 34 subjects completed the test.

Method: A webril/adhesive patch was used semi-occlusively. Approximately 0.2 ml of each Test Material was applied to each designated patch. Each subject was patched and instructed that the patches were to remain in place and dry.

Approximately 48 hours after each patching (approximately 72 hours on the weekend) the patches were removed at SGS and the test sites were scored by the SGS technician (see Scoring system below). The scores obtained for the test sites were recorded on the subject's individual Data Form. Fresh patches were then re-applied immediately.

The Test Materials were applied to the same sites on the back, at the rate of three times weekly for six (6) applications within a 14 day period.

Scoring system, as shown below: The test sites were scored using the modified scoring scale of the International Contact Dermatitis Research Group System: Fisher, Alexander A., Contact Dermatitis, Lea & Febiger, Philadelphia, 2008: p 27. As per the protocol, if severe irritation had been observed on any site (Grade 3 or 4 and/or edema), no further application(s) would have been made to that site, and the maximum score would have been assigned to that Test Material/site for the duration of the test.

Results: See Table 9, below. No adverse reactions or adverse events related to the Test Materials were exhibited/reported by any subject during this test. Erythema, edema, dryness, staining, peeling and hyperpigmentation/hypopigmentation are possible, expected endpoints and not considered Adverse Reactions. This test was conducted under the supervision of a Board-Certified Dermatologist, a Co-Investigator. A total of 34 subjects, 9 male and 25 female, completed the test. Subjects range in age from 20-67.

The six (6) daily scores for a given test material on a test subsite are summed to yield an aggregate score. A Grand Total Score for a test material is obtained by summing the totals for all subjects. Note that, using 4 as the maximum daily score, the maximum score per evaluation for 34 subjects would be 136 and the Potential Maximum Total Score for 6 evaluations would be 816. Thus, if the Grand Total Scores are used, the minimum would be 0 with a maximum of 816.

The Potential Maximum Total Score is 816 for each Test Material for the subjects who completed the test.

No adverse reactions or adverse events were reported/observed in any of the subjects.

Conclusion: The Potential Maximum Total Score for the subjects who completed the test is 816 for each test material.

TABLE 9

Summary of results for Cumulative Irritation Test for formulations

| TEST MATERIAL | GRAND TOTAL SCORE | CONCLUSION |
|---|---|---|
| Cumulative Irritation Test-Lash and Brow Serum Formulation C | 13.5E | negligible cumulative* irritation |
| Cumulative Irritation Test-Eye-gel cream Formulation B | 0 | no cumulative irritation |
| Cumulative Irritation Test-Micellar makeup remover Formulation F | 29.5E | minimal cumulative* irritation |
| Cumulative Irritation Test-Micellar makeup remover Formulation E | 2.0 | negligible cumulative** irritation |
| Cumulative Irritation Test-Lash and Brow Serum D | 0.5 | negligible cumulative irritation |
| Olay for Bright Eyes | 6.5 | negligible cumulative irritation |
| Loreal Lash Serum Solution | 1.0 | negligible cumulative irritation |
| Negative control (Saline) | 0 | no cumulative irritation |
| 0.5% Sodium Lauryl Sulfate | 99 | moderate cumulative irritation |

*Although negligible or minimal per calculation, 2.9% (1/34) of the panelists showed robust reaction (>1E) which is significant for cosmetic products. Sponsor is advised to re-test the test material to ensure their safety.
**Grand total score was calculated based on 33 subjects who completed the study.

Scoring criteria

| | Reaction | Cumulative Irritation Index 25 finish | Cumulative Irritation Index 34 finish |
|---|---|---|---|
| Index value | | 1 | 1.36 |
| no cumulative irritation | ± and/or 1 | 0 | 0 |
| negligible cumulative irritation | ± and/or 1 | 0.5-10.0 | 0.5-13.6 |
| minimal cumulative irritation | ± and/or 1 | 10.5-35.0 | 13.7-47.6 |
| moderate cumulative irritation | ± and/or 1 | 35.5-99.5 | 47.7-135.32 |
| significant cumulative irritation | 2-level or higher and/or edematous reaction | >100 | >136 |

What is claimed:

1. An eye formulation comprising:

alexidine hydrochloride, two or more plant extracts including *Euphrasia officinalis* extract and *Glycyrrhiza glabra* root extract, and niacinamide, panthenol, and sodium ascorbyl phosphate;

wherein the formulation does not induce dermal sensitization of the skin to which it is applied.

2. The eye formulation according to claim 1, wherein the formulation passes a Repeated Insult Patch Test.

3. The eye formulation according to claim 1, wherein the formulation is an eye gel-cream, a lash and brow formulation, a micellar cleansing formulation, an eye illumination formulation, and/or an eye conditioning formulation.

4. The eye formulation according to claim 1, wherein the formulation does not comprise a fragrance.

5. The eye formulation according to claim 1, wherein the formulation does not comprise any animal-derived ingredients.

6. The eye formulation according to claim 1, wherein the formulation does not comprise any petroleum-derived ingredients.

7. The eye formulation according to claim 1, wherein the formulation does not contain any parabens, thiazolinones, and/or formaldehyde-donor preservatives.

8. The eye formulation according to claim 1, wherein the formulation does not contain polyethylene glycol (PEG) or any PEG-containing ingredients.

9. The eye formulation according to claim 1, wherein the formulation further comprises at least one natural humectant.

10. The eye formulation according to claim 1, wherein the formulation further comprises at least one additional plant extract chosen from caffeine, *Gleditsia triacanthos* seed extract, and *butyrospermum parkii* butter.

11. The eye formulation according to claim 1, wherein the formulation further comprises at least one buffer.

12. The eye formulation according to claim 1, wherein the formulation further comprises at least one additional vitamin is chosen from biotin, ascorbate, tetrahexyldecyl ascorbate, and tocopheryl acetate.

13. The eye formulation according to claim 1, wherein the formulation comprises:

Water;
Isohexadecane;
Squalane;
Glycerin;
Niacinamide;
Sodium ascorbyl phosphate;
Sodium Hyaluronate;
Decyl glucoside;
Panthenol;
Sodium Chloride USP;
Potassium Chloride USP;
Sodium Citrate USP Dihydrate;
Disodium EDTA, dihydrate;
*Glycyrrhiza glabra* Root Extract;
*Euphrasia officinalis* Extract;
Citric acid USP, anhydrous; and
Alexidine Hydrochloride.

14. The eye formulation according to claim 1, wherein the formulation comprises:

about 90% w/w Water;
about 5.6% w/w Isohexadecane;
about 1.9% w/w Squalane;
about 0.7% w/w Glycerin, and optionally additional Glycerin as a component in the plant extracts in an amount of about <0.19% w/w;
about 0.7% w/w Niacinamide;
about 0.3% w/w Sodium ascorbyl phosphate;
about 0.1% w/w Sodium Hyaluronate;
about 0.1% w/w Decyl glucoside;
about 0.1% w/w Panthenol;
about 0.1% w/w Sodium Chloride USP;
about 0.1% w/w Potassium Chloride USP;
about 0.1% w/w Sodium Citrate USP Dihydrate;
about 0.1% w/w Disodium EDTA, dihydrate;
about <0.1% w/w *Glycyrrhiza glabra* Root Extract;
about <0.1% w/w *Euphrasia officinalis* Extract;
about 0.02% w/w Citric acid USP, anhydrous; and
about 0.001% w/w Alexidine Hydrochloride.

* * * * *